United States Patent
Suga et al.

(10) Patent No.: US 9,433,483 B2
(45) Date of Patent: Sep. 6, 2016

(54) IMPRESSION TRAY SET FOR EDENTULOUS JAW

(71) Applicant: GC Corporation, Tokyo (JP)

(72) Inventors: Takeo Suga, Kanagawa (JP); Masataka Itoda, Osaka (JP); Hiroshi Kamohara, Tokyo (JP)

(73) Assignee: GC Corporation, Tokyo (JP)

( * ) Notice: Subject to any disclaimer, the term of this patent is extended or adjusted under 35 U.S.C. 154(b) by 25 days.

(21) Appl. No.: 14/407,532

(22) PCT Filed: Jun. 17, 2013

(86) PCT No.: PCT/JP2013/066571
§ 371 (c)(1),
(2) Date: Dec. 12, 2014

(87) PCT Pub. No.: WO2013/191126
PCT Pub. Date: Dec. 27, 2013

(65) Prior Publication Data
US 2015/0150657 A1    Jun. 4, 2015

(30) Foreign Application Priority Data
Jun. 22, 2012 (JP) ................................ 2012-141176

(51) Int. Cl.
*A61C 9/00* (2006.01)
*A61C 8/00* (2006.01)
*A61C 19/05* (2006.01)

(52) U.S. Cl.
CPC ........... *A61C 9/0006* (2013.01); *A61C 8/0001* (2013.01); *A61C 19/05* (2013.01)

(58) Field of Classification Search
CPC .......................................... A61C 9/00–9/0093
USPC .............................. 433/34–48, 213
See application file for complete search history.

(56) References Cited

U.S. PATENT DOCUMENTS 2,618,853 A * 11/1952 Singer .................... A61C 19/05
433/69
2,708,789 A    5/1955 Opotow
(Continued)

FOREIGN PATENT DOCUMENTS

DE    3239529    5/1984
EP    0109578    5/1984
(Continued)

OTHER PUBLICATIONS

International Search Report mailed on Jul. 16, 2013.

*Primary Examiner* — Yogesh Patel
(74) *Attorney, Agent, or Firm* — IPUSA, PLLC

(57) ABSTRACT

An impression tray set for edentulous jaw is formed by a maxillary impression tray and a mandibular impression tray respectively including a tray main body having a U-shaped groove on which an impression material is to be applied on a front surface thereof, an engaging part formed on a back surface of the U-shaped groove in a position corresponding to an alveolar ridge of front teeth, and a handle part detachably connected to the engaging part. Each of the maxillary and mandibular impression trays includes projecting parts provided on the back surface at portions corresponding to an alveolar ridge from a first molar part to a premolar part. The projecting parts determine bite position and height in a state in which at least a part of flat top surfaces of the projecting parts contact each other when taking an impression.

2 Claims, 5 Drawing Sheets

(56) References Cited

U.S. PATENT DOCUMENTS

| | | | |
|---|---|---|---|
| 4,235,594 A * | 11/1980 | Schwartz | A61C 19/05 433/213 |
| 5,076,785 A * | 12/1991 | Tsai | A61C 9/0006 433/46 |
| 5,752,826 A | 5/1998 | Andreiko | |
| 6,196,840 B1 | 3/2001 | Zentz et al. | |
| 6,315,555 B1 | 11/2001 | Bortolotti | |
| 2010/0075273 A1 | 3/2010 | Karlsson et al. | |

FOREIGN PATENT DOCUMENTS

| | | |
|---|---|---|
| JP | S50-033688 | 3/1975 |
| JP | H06-078937 | 3/1994 |
| JP | H07-023984 | 1/1995 |
| JP | H08-266561 | 10/1996 |
| JP | 2001-333917 | 12/2001 |
| JP | 2002-522151 | 7/2002 |
| JP | 2010-507446 | 3/2010 |
| WO | 00/09032 | 2/2000 |

* cited by examiner

IMPRESSION TRAY SET FOR EDENTULOUS JAW

TECHNICAL FIELD

The present invention relates to an impression tray set for edentulous jaw, including a pair of a maxillary impression tray and a mandibular impression tray for use in taking an intraoral impression, and capable of simultaneously recording bite position and height when taking the impression.

BACKGROUND ART

Generally, in odontotherapy, when taking an intraoral impression in a preparation stage of manufacturing prostheses, an impression material such as silicone impression materials, alginate impression materials, and the like is used. An impression tray is used to intraorally hold such an impression material. The impression material is applied on the impression tray that is inserted into an oral cavity of a patient, and after the impression material is pressed for taking an impression and is set, the impression tray is removed from the oral cavity of the patient in a state in which the set impression material is integrally held on the impression tray.

When taking such an impression from an edentulous patient (including a substantially edentulous patient), the impression must be taken from an alveolar ridge that forms a smooth curve. In this case, an extremely high accuracy is required, such as when pressing the impression material against the alveolar ridge with a uniform force.

For this reason, in order to more accurately take the intraoral impression, the impression is in many cases taken twice from the edentulous patient.

More particularly, a first impression is taken from the alveolar ridge by first using a general impression tray, and an edentulous jaw model is thereafter manufactured from the set impression material. Then, an impression tray (hereinafter referred to as a personal tray) exclusively for the edentulous patient is manufactured from the edentulous jaw model.

Next, the impression material is thinly applied on the personal tray, and a second impression is taken from the alveolar ridge, in order to manufacture a more accurate edentulous jaw model from the impression.

In the case of an edentulous patient, bite position and height must be determined separately because the edentulous patient has no teeth. Hence, a large number of processes, including measurements made from outside the face using a measuring apparatus and the like, determining the bite position and height by reflecting measured data to the edentulous jaw model on an articulator, and the like, are carried out in order to finally manufacture a full denture base.

As the impression tray for use in taking the impression from the edentulous patient, there is an impression tray for maxillary mucosa of the edentulous patient, applied with an utility wax, and including a peripheral wall part having an edge that makes contact with each mucosa at a bottom of a valley-shaped part between a cheek and a maxillary alveolar ridge of the patient having the edentulous alveolar ridge, and at an inner part of an maxillopalatine lower surface, a bottom plate part connected to a large portion of an edge on an opposite side from the edge of the peripheral wall part and provided with an impression material injection opening only at a part near the alveolar ridge at a front part of the peripheral wall part, and a handle provided on the front part of the peripheral wall part (refer to Patent Document 1, for example).

This impression tray for maxillary mucosa is for use in supplying and setting a slurry of a plaster impression material in order to take an accurate impression in a non-pressure state, and is applied with the utility wax so that the slurry of the impression material does not drop or leak from the impression tray (refer to paragraphs 0002-0005 of specification of Patent Document 1), and the impression only needs to be taken once.

However, this impression tray is merely for taking the impression of the alveolar ridge (refer to paragraph 0001 of specification of Patent Document 1), and no data can be obtained with respect to the bite position and height. For this reason, the full denture base cannot be manufactured by simply taking the impression using this impression tray, and as in the conventional case, the bite position and height must be determined through separate measurements and the like.

PRIOR ART DOCUMENTS

Patent Documents

Patent Document 1: Japanese Laid-Open Patent Publication No. H07-23984 (1995-023984)

DISCLOSURE OF THE INVENTION

Problem to be Solved by the Invention

One object of the present invention is to provide an impression tray set for edentulous jaw, including a pair of a maxillary impression tray and a mandibular impression tray for use in taking an intraoral impression of a patient including an edentulous patient, and capable of simultaneously recording bite position and height when taking the impression.

Means of Solving the Problem

As a result of diligent research conducted to solve the problem described above, the present inventors found that when an impression tray set for edentulous jaw includes a maxillary impression tray and a mandibular impression tray respectively including a tray main body having a U-shaped groove on which an impression material is to be applied on a front surface side thereof, an engaging part formed on a back surface of the U-shaped groove in a position corresponding to an alveolar ridge of front teeth, and a handle part that is detachably connected to the engaging part, the handle part can be removed when taking an impression using the impression tray set, and it is possible to prevent an inaccurate impression caused by the handle part hitting a lip. In addition, the present inventors found that when each of the maxillary impression tray and the mandibular impression tray includes projecting parts on the back surface, at left and right portions of the U-shaped groove in a position corresponding to an alveolar ridge from a first molar part to a premolar part, and the projecting parts is to be used for determining bite position and height in a state which at least a part of flat top surfaces of the projecting parts contact each other when taking an impression, a pair of projecting parts can be arranged on the left and right at approximately an intermediate part between the front teeth and the molars. Hence, the present inventors also found that by adjusting positions in a state in which at least a part of the flat top surfaces of the projecting parts contact each other, positions of the maxillary impression tray and the mandibular impression tray can be determined at various bite positions and heights, and that processes that need to be carried out separately, such as measuring the bite position and height, can be omitted, and a full denture base can be manufactured quickly and with ease. The present inventors completed the present invention based on these findings.

In other words, an impression tray set for edentulous jaw, comprising a maxillary impression tray and a mandibular impression tray respectively including a tray main body having a U-shaped groove on which an impression material is to be applied on a front surface side thereof, an engaging part formed on a back surface of the U-shaped groove in a position corresponding to an alveolar ridge of front teeth, and a handle part that is detachably connected to the engaging part, is characterized in that each of the maxillary impression tray and the mandibular impression tray includes a pair of projecting parts being provided on the back surface, at left and right portions of the U-shaped groove in a position corresponding to an alveolar ridge from a first molar part to a premolar part, the projecting parts are to be used for determining bite position and height in a state in which at least a part of flat top surfaces of the projecting parts contact each other when taking an impression.

When determining the bite position and height, the top surfaces of the projecting parts of the maxillary impression tray and the mandibular impression tray do not necessarily become parallel as illustrated in FIG. 6 (explanatory side view with the impression material omitted). Hence, in order to more easily cope with various cases, the projecting part is preferably formed so that a longitudinal direction thereof matches a ridge line direction at the back surface of the U-shaped groove as illustrated in FIG. 3, a length thereof in the longitudinal direction is 5 mm to 20 mm, and a width in a width direction is 3 mm to 10 mm. In this case, it is possible to prevent a state in which the maxillary and mandibular projecting parts do not make contact due to the patient's jaw position. Furthermore, when relatively small projecting parts are used, the projecting parts can more easily be moved even to the bite position and height where the projecting parts are inclined and held at the inclined position illustrated in FIG. 7 (explanatory side view with the impression material omitted). In addition, when the projecting part is formed by a hollow tubular part integrally formed on each of the maxillary impression tray and the mandibular impression tray, and a bite height adjusting piece that is inserted into and retained within a hole part of the tubular part and has a part corresponding to the top surface, the height of the projecting part can be changed with ease, and it is preferable in that accurate bite position and height can easily be determined.

Effects of the Invention

An impression tray set for edentulous jaw according to the present invention includes a maxillary impression tray and a mandibular impression tray respectively including a tray main body having a U-shaped groove on which an impression material is to be applied on a front surface side thereof, an engaging part formed on a back surface of the U-shaped groove in a position corresponding to an alveolar ridge of front teeth, and a handle part that is detachably connected to the engaging part. Because the handle part can be removed when taking an impression using the impression tray set, and it is possible to prevent an inaccurate impression caused by the handle part hitting a lip. In addition, each of the maxillary impression tray and the mandibular impression tray includes projecting parts being provided on the back surface, at left and right portions of the U-shaped groove in a position corresponding to an alveolar ridge from a first molar part to a premolar part, the projecting parts being used for determining bite position and height in a state in which at least a part of flat top surfaces of the projecting parts contact each other when taking an impression, a pair of projecting parts can be arranged on the left and right at approximately an intermediate part between the front teeth and the molars. Hence, by adjusting positions in a state in which at least a part of the flat top surfaces of the projecting parts contact each other, positions of the maxillary impression tray and the mandibular impression tray can be determined at various bite positions and heights, and processes that need to be carried out separately, such as measuring the bite position and height, can be omitted, and the full denture base can be manufactured quickly and with ease. Further, when the handle part is removed when taking the impression, the impression material can easily be pressed against the alveolar ridge by pushing the projecting parts by fingers, without causing the excess impression material to stick to a hand.

In the above described configuration, when the projecting part is formed so that a longitudinal direction thereof matches a ridge line direction at the back surface of the U-shaped groove, a length thereof in the longitudinal direction is 5 mm to 20 mm, and a width in a width direction is 3 mm to 10 mm, it is possible to prevent a state in which the maxillary and mandibular projecting parts do not make contact due to the patient's jaw position. Furthermore, when relatively small projecting parts are used, it is preferable in that the projecting parts can more easily be moved even to the bite position and height where the projecting parts are inclined and held at the inclined position. In addition, when the projecting part is formed by a hollow tubular part integrally formed on each of the maxillary impression tray and the mandibular impression tray, and a bite height adjusting piece that is inserted into and retained within a hole part of the tubular part and has a part corresponding to the top surface, the height of the projecting part can be changed with ease, and it is preferable in that accurate bite position and height can easily be determined.

MODE OF CARRYING OUT THE INVENTION

Figure 1:
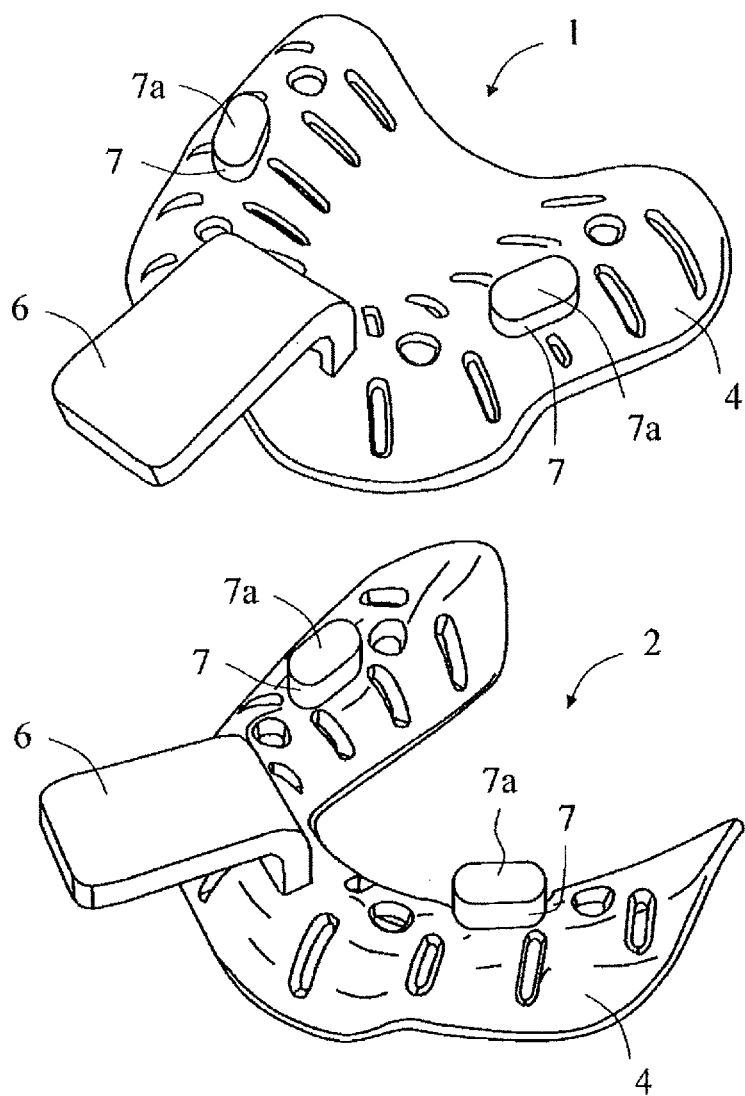
FIG. 1 is a perspective view illustrating one embodiment of an impression tray set for edentulous jaw according to the present invention.
Figure 2:
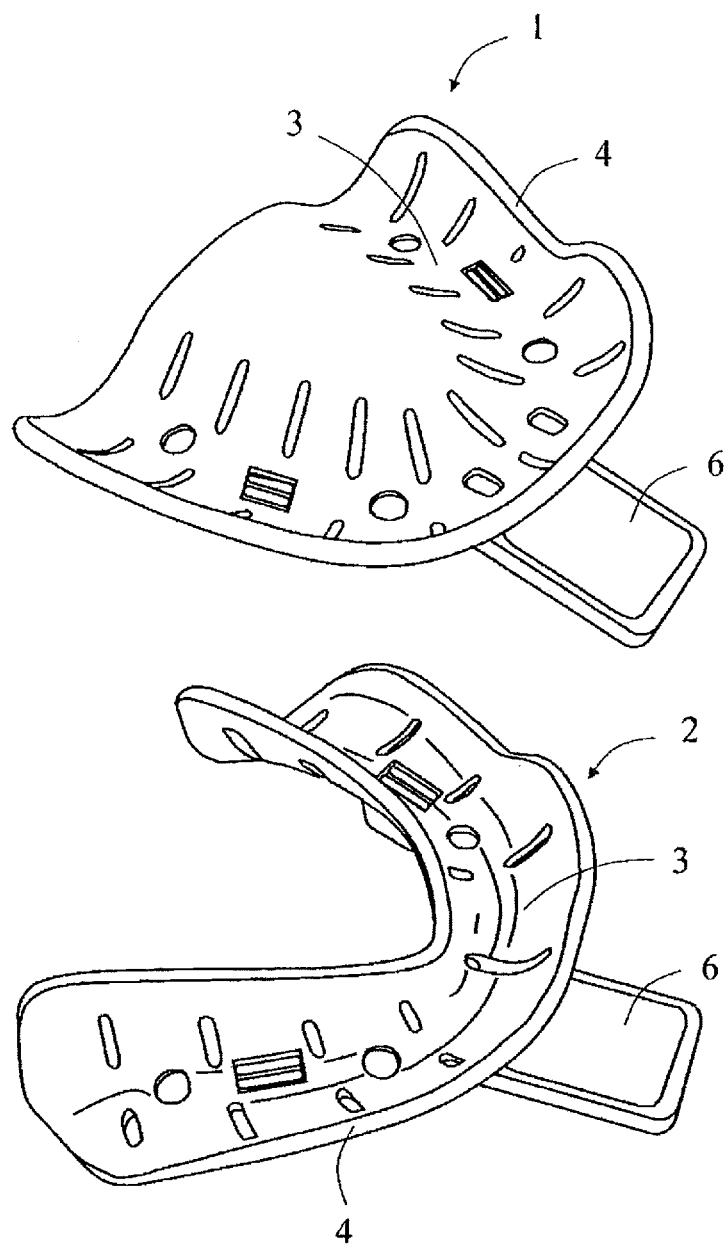
FIG. 2 is a perspective view illustrating the impression tray set for edentulous jaw illustrated in FIG. 1 viewed from a front surface side.
Figure 3:
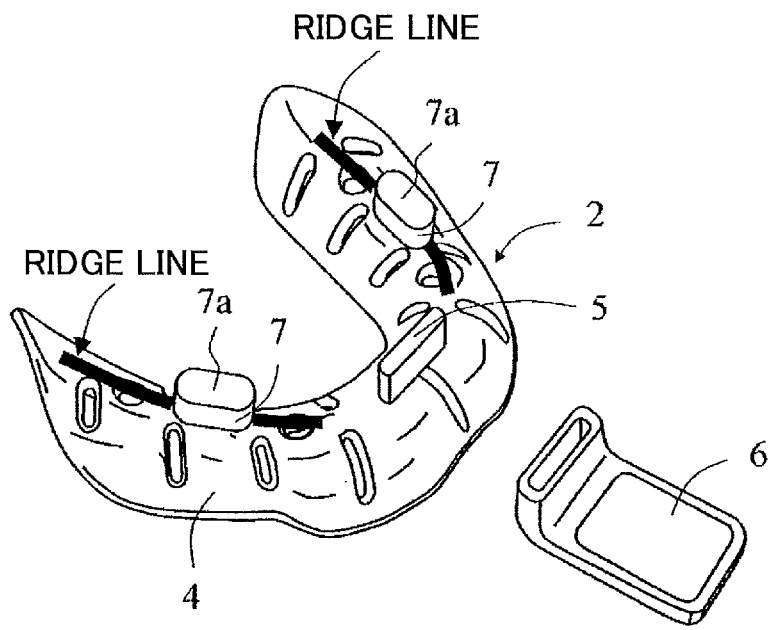
FIG. 3 is a perspective view illustrating a mandibular impression tray illustrated in FIG. 1 in a state in which a handle part is removed.

A detailed description will hereinafter be given of the impression tray set for edentulous jaw according to the present invention, by referring to the drawings.

In the drawings, an impression tray set for edentulous jaw according to the present invention is formed by a maxillary impression tray 1 and a mandibular impression tray 2. Each of the maxillary impression tray 1 and the mandibular impression tray 2 is formed by a tray main body 4 and a handle part 6 which will be described later.

A U-shaped groove 3 is to be used for being applied with an impression material thereon. And the tray main body 4 has the U-shaped groove 3 on a front surface side thereof. As illustrated in FIGS. 1-7, the tray main body 4 is preferably formed with elongated holes and the like through which the impression material is pushed out and combined into one piece. In addition, as illustrated in FIGS. 1-5, the mandibular impression tray 2 needs to have a shape that does not have a part corresponding to a tongue part.

An engaging part 5 is formed on a back surface of the U-shaped groove 3 in a position corresponding to an alveolar ridge of front teeth. And the handle part 6 is detachably connected to the engaging part 5.

Projecting parts 7 are to be used for determining bite position and height in a state in which at least a part of flat top surfaces 7a of the projecting parts 7 contact each other when taking an impression. The projecting parts 7 are provided on the back surface of each of the maxillary impression tray 1 and the mandibular impression tray 2, at left and right portions of the U-shaped groove 3 in a position corresponding to the alveolar ridge from a first molar part to a premolar part.

When the projecting part 7 is formed so that a longitudinal direction thereof matches a ridge line direction at the back surface of the U-shaped groove 3, and a length thereof in the longitudinal direction is 5 mm to 20 mm and a width in a width direction is 3 mm to 10 mm, it is possible to prevent a state in which the maxillary and mandibular projecting parts do not make contact due to the patient's jaw position. Furthermore, when relatively small projecting parts are used, it is preferable in that the projecting parts can easily be moved even to the bite position and height where the projecting parts are inclined and held at the inclined position.

The longitudinal length of the projecting part 7 is set to 5 mm to 20 mm, because when the longitudinal length is less than 5 mm, the projecting part 7 is too short, and it may not be easy to make at least a part of the flat top surfaces 7a of the projecting parts 7 of the maxillary impression tray 1 and the mandibular impression tray 2 contact each other when determining the bite position and height. On the other, when the longitudinal length of the projecting part 7 exceeds 20 mm, the projecting part 7 is too long, and it becomes not easy to tilt the top surface 7a or maintain the position of the projecting part 7. Moreover, the width of the projecting part 7 is set to 3 mm to 10 mm, because when the width of the projecting part 7 is less than 3 mm, the projecting part 7 is too narrow, and it may not be easy to make at least a part of the flat top surfaces 7a of the projecting parts 7 contact each other when determining the bite position and height. On the other hand, when the width of the projecting part 7 exceeds 10 mm, the projecting part 7 is too wide, and an inconvenience such as the projecting part 7 hitting the cheek may occur.

Figure 4:
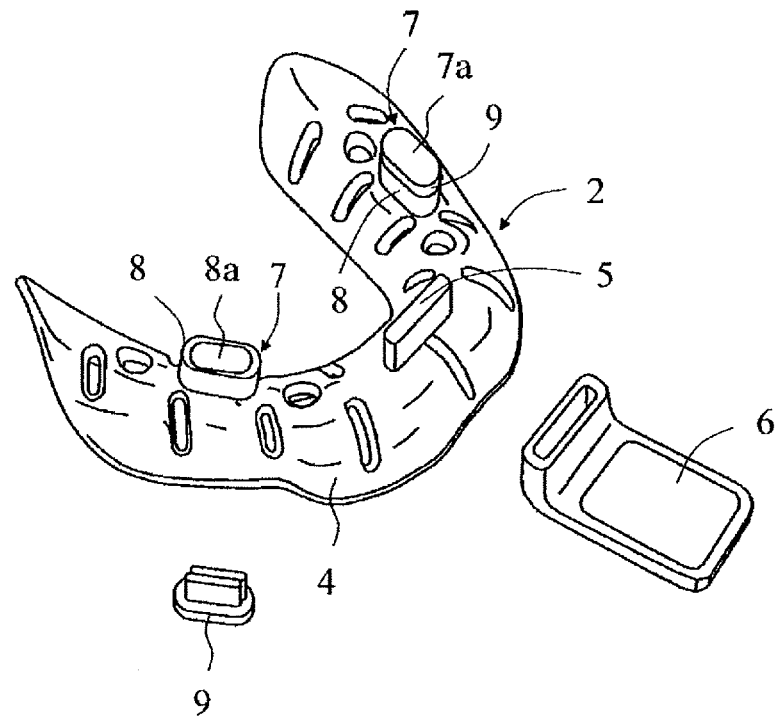
FIG. 4 is a perspective view illustrating a mandibular impression tray in another embodiment of the impression tray set for edentulous jaw according to the present invention.
Figure 5:
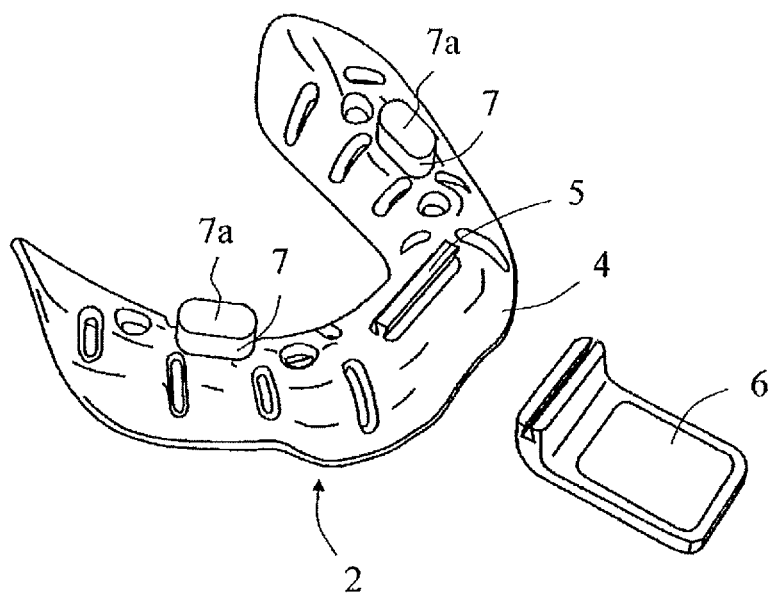
FIG. 5 is a perspective view illustrating a mandibular impression tray in still another embodiment of the impression tray set for edentulous jaw according to the present invention.
Figure 6:
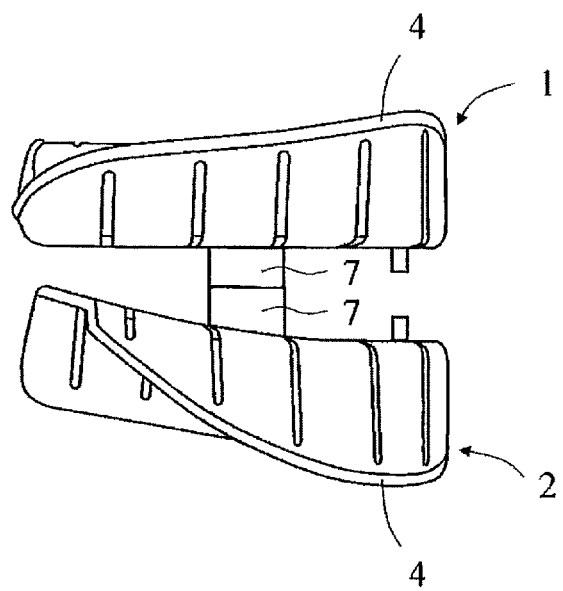
FIG. 6 is an explanatory side view illustrating a state in which the handle parts are removed from the impression tray set for edentulous jaw illustrated in FIG. 1 and top surfaces of projecting parts of the impression trays make contact in a state in which the top surfaces are parallel.
Figure 7:
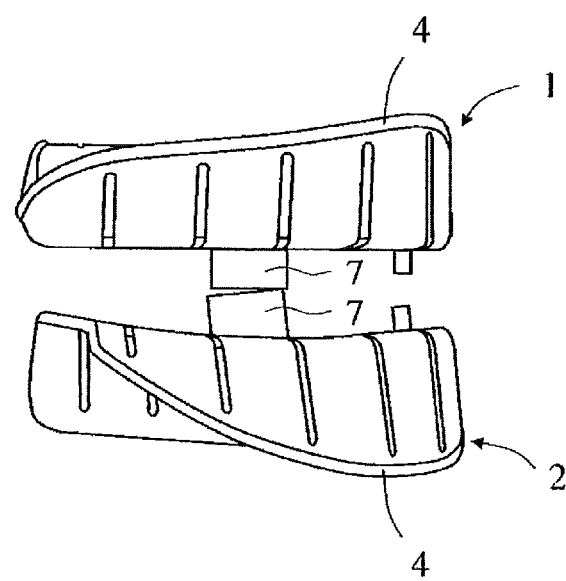
FIG. 7 is an explanatory side view illustrating a state in which the handle parts are removed from the impression tray set for edentulous jaw illustrated in FIG. 1 and the top surfaces of the projecting parts of the impression trays make partial contact in a state in which the top surfaces are inclined.

A tubular part 8 is hollow-shaped and is integrally formed on each of the maxillary impression tray 1 and the mandibular impression tray 2. A bite height adjusting piece 9 is to be inserted into and retained within a hole part 8a of the tubular part 8, and has a part corresponding to the top surface 7a. For example, two protrusions on the bite height adjusting piece 9 may make contact with an inner surface defining the hole part 8a of the tubular part 8, as illustrated in FIG. 4, in order to retain the bite height adjusting piece 9 within the hole part 8a.

When the projecting part 7 is formed by the tubular part 8 and the bite height adjusting piece 9, the height of the projecting part 7 can be changed with ease, and it is preferable in that accurate bite position and height can easily be determined.

When actually using the impression tray set for edentulous jaw according to the present invention described above, an impression material is first applied in each of the U-shaped grooves 3 of the maxillary impression tray 1 and the mandibular impression tray 2, and the impression material applied thereon is pressed against the alveolar ridge within the oral cavity and set. In addition, the bite position and height are determined while making at least a part of the flat top surfaces 7a of the projecting parts 7 contact each other.

In a case in which the impression is taken in the above described manner, the impression may be taken carefully once, or the impression may be taken twice for more accuracy. Even in the case in which the impression is taken twice, it is not a precondition in the impression tray set for edentulous jaw according to the present invention to manufacture a personal tray. Hence, after the first impression is taken by the maxillary impression tray 1 and the mandibular impression tray 2, the impression material is thinly and newly applied on the top surface of the impression material on the impression trays 1 and 2, in order to take the second impression.

When taking the impression in this manner, the patient is urged to bite while gradually moving the maxillary impression tray 1 and the mandibular impression tray 2 within the oral cavity, in order to look for an appropriate bite position and height at the position where the top surfaces 7a of the projecting parts 7 of the maxillary impression tray 1 and the mandibular impression tray 2 make contact with each other.

In this case, the bite position and height may be determined after the impression material applied on the maxillary impression tray 1 and the mandibular impression tray 2 in a state in which the impression material is sufficiently set, or the bite position and height may be determined in a state in which the impression material is not yet completely set.

After the impression material is pressed against the alveolar ridge within the oral cavity and set and the bite position and height are determined in the above described manner, the impression material is applied between the back surfaces of the maxillary impression tray 1 and the mandibular impression tray 2 and set in the state in which the flat top surfaces 7a of the projecting parts 7 of the impression trays 1 and 2 make contact with each other. Hence, the positions of the maxillary impression tray 1, the mandibular impression tray 2, and the impression material applied therebetween are fixed, and the determined bite position and height can be recorded.

The impression trays 1 and 2 and the impression material, whose positions are fixed, are removed from within the oral cavity in one piece of the maxillary and mandibular impression trays, or separately in two pieces of the maxillary and mandibular impression trays. Thereafter, a model material is injected to each impression material on the removed maxillary and mandibular impression trays and set, in order to manufacture an edentulous jaw model.

This edentulous jaw model is set on an articulator based on the bite position and height that are recorded in advance, and a full denture base can thereafter be manufactured according to a known method. Hence, processes conventionally carried out to determine the bite position and height can be omitted, and the full denture base can be manufactured quickly and with ease.

DESCRIPTION OF REFERENCE NUMERALS

1 Maxillary Impression Tray
2 Mandibular Impression Tray
3 U-shaped Groove
4 Tray Main Body
5 Engaging Part
6 Handle Part
7 Projecting Part
7a Top Surface
8 Tubular Part
8a Hole Part
9 Bite Height Adjusting Piece

The invention claimed is:

1. An impression tray set for edentulous jaw, comprising:
a maxillary impression tray and a mandibular impression tray respectively including a tray main body having a U-shaped groove on which an impression material is to be applied on a front surface side thereof, an engaging part formed on a back surface of the U-shaped groove in a position corresponding to an alveolar ridge of front teeth, and a handle part that is detachably connected to the engaging part,
wherein each of the maxillary impression tray and the mandibular impression tray includes projecting parts provided on the back surface, at left and right portions of the U-shaped groove at a position corresponding to an alveolar ridge from a first molar part to a premolar part,
wherein the projecting parts are used for determining bite position and height in a state in which at least a part of flat top surfaces of the projecting parts contact each other when taking an impression, and
wherein each of the projecting parts includes a hollow tubular part integrally formed on each of the maxillary impression tray and the mandibular impression tray, and a bite height adjusting piece that is inserted into and retained within a hole part of the hollow tubular part and has a part corresponding to one of the flat top surfaces.

2. The impression tray set for edentulous jaw as claimed in claim 1, wherein the projecting part is formed so that a longitudinal direction thereof matches a ridge line direction at the back surface of the U-shaped groove, a length thereof in the longitudinal direction is 5 mm to 20 mm, and a width in a width direction is 3 mm to 10 mm.

* * * * *